(12) United States Patent
Gitis et al.

(10) Patent No.: US 6,969,392 B2
(45) Date of Patent: Nov. 29, 2005

(54) MULTIPORTAL DEVICE AND METHOD FOR PERCUTANEOUS SURGERY

(75) Inventors: Norm Gitis, Cupertino, CA (US); Todd F. Alamin, San Mateo, CA (US); Aleksandr Meyman, Belmont, CA (US); Oleg Shulepov, Santa Clara, CA (US); Mikhail Faynberg, San Jose, CA (US)

(73) Assignee: Nevmet Corporation, Reno, NV (US)

( * ) Notice: Subject to any disclaimer, the term of this patent is extended or adjusted under 35 U.S.C. 154(b) by 592 days.

(21) Appl. No.: 10/136,548

(22) Filed: May 1, 2002

(65) Prior Publication Data

US 2003/0208206 A1    Nov. 6, 2003

(51) Int. Cl.[7] .............................................. A61B 17/90
(52) U.S. Cl. .......................................... 606/87; 606/96
(58) Field of Search .............................. 604/533, 538, 604/240–242, 510; 606/87, 108; 600/114

(56) References Cited

U.S. PATENT DOCUMENTS

| | | | |
|---|---|---|---|
| 3,299,883 A | * | 1/1967 | Rubens ....................... 600/102 |
| 4,545,374 A | | 10/1985 | Jacobson |
| 5,084,043 A | | 1/1992 | Hertzmann et al. |
| 5,301,658 A | * | 4/1994 | Zhu et al. .................... 606/191 |
| 5,437,661 A | | 8/1995 | Rieser |
| 5,531,751 A | * | 7/1996 | Schultheiss et al. .......... 606/96 |
| 5,643,273 A | * | 7/1997 | Clark ........................... 606/96 |
| 5,730,754 A | | 3/1998 | Obenchain |
| 5,762,629 A | | 6/1998 | Kambin |
| 5,797,835 A | * | 8/1998 | Green .......................... 600/106 |
| 5,957,832 A | * | 9/1999 | Taylor et al. ................ 600/114 |
| 6,228,022 B1 | | 5/2001 | Friesem et al. |
| 6,254,553 B1 | | 7/2001 | Lidgren et al. |
| 6,264,650 B1 | | 7/2001 | Hovda et al. |

OTHER PUBLICATIONS

Clinical Orthopaedics and Related Research, No. 238, 1989. (by A. Shzeiber et al).

* cited by examiner

Primary Examiner—Julian W. Woo
Assistant Examiner—Sarah Webb

(57) ABSTRACT

A multiportal device for percutaneous surgery consists of a guiding device with a radial arm that supports an auxiliary guiding device, which can slide along the arm and can be fixed in a require angular position on the arm. The device also includes a first cannula, which can be inserted into the patient's body through the guiding device and can be fixed in a required axial position, and a second cannula, which can be inserted into the second guiding unit and fixed therein. The arch-shaped form of the arm ensures intersection of distal ends of both cannulae in one point aimed at the symptomatic site where surgery has to be done. The device is provided with a linking mechanism that links the distal ends of both cannulae in their position inside the body of a patient. In the engaged state of the linking device, the cannulae still have some freedom of relative movements that may be required for manipulation with cannulae during the surgery. The invention also relates to a method of using the multiportal device for percutaneous surgery. The device allows insertion of a plurality of cannulae and permanently maintaining them in controlled positions without resorting to additional X-ray.

14 Claims, 16 Drawing Sheets

MULTIPORTAL DEVICE AND METHOD FOR PERCUTANEOUS SURGERY

FIELD OF THE INVENTION

This invention relates to the field of medicine, in particular to surgery, and specifically to a method and a device for access and removal of prolapsed nucleus pulposus material of a herniated intervertebral disc through the spinal foramen.

BACKGROUND OF THE INVENTION

Low back pain and radiculopathy as a result of herniated intervertebral disc represents a major health problem in the United States and all over the world. About 300,000 Americans and about the same number of people throughout the world outside the USA are operated upon each year due to this problem. Even many more people might benefit from surgical help, as those that undergo the surgery represent only about 20% of those with cervical pathology referable to the intervertebral disc.

An intervertebral disc is a structure that occupies the space between the vertebrae. It serves, in particular, as a load-absorbing cushion.

FIG. 1 is a cross-sectional view of a vertebral column through a healthy intervertebral disc 20, and FIG. 2 is a side view on a part of the vertebral column illustrating the position of the disc 20. As can be seen from FIGS. 1 and 2, the disc 20 consists of two parts: a ring-like external part 22, known as "annulus" (or "annulus fibrosis"), and an internal, central part 24, known as "nucleus" (or "nucleus pulposus"). The tissue of the annulus 22 degenerates with age or as a result of some injuries, or illnesses. When annulus 22 degenerates, its fibers weaken, and external forces applied to the adjacent vertebrae, can cause the rupture of the annulus fibers and nucleus tissue protrusion, shown in FIGS. 3 and 4 that correspond respectively to FIGS. 1 and 2. This creates a disc herniation 26 (FIG. 3), which, in turn, may cause a pressure on the adjacent nerve root 28 (FIGS. 1 and 3), resulting in pain.

It is understood that herniation may occur in any other part of the disc and cause different symptoms and that the herniation position shown in FIGS. 3 and 4 is given just as an example.

At the present time, several approaches exist for treatment of the problem described above. The first method is called "laminectomy". This is a surgical procedure, which involves accessing a symptomatic disc by excising a significant amount of the vertebral lamina, followed by removal of the herniated disc material. A laminectomy is a somewhat destructive procedure, which might cause extensive scarring and long (up to 9 days) hospitalization, with an up to 3-month postoperative recovery period.

Another approach is called "microlumbar surgery" ("microsurgical discectomy", or "microdiscectomy"). It is similar to laminectomy in that the disc is accessed through an incision, made on the patient's back and developed into a channel to the symptomatic disc. Unlike laminectomy, the microdiscectomy employs a microscope, allowing a smaller incision (about 2 times less than during the laminectomy). This method permits the surgeon to use microsurgical tools, and avoid much of the bone dissection. This is less invasive compared to the laminectomy, though the existing microdiscectomy may still cause some complications similar to those associated with laminectomy, for example, possible injury to the nerve root and dural sac, postoperative scarring and relatively long recovery time. Furthermore, the paraspinal musculature must still be retracted out to the level of the facet for the duration of the procedure.

Other methods of treatment consist of a removal of the disc nucleus tissue either by suction or by dissolving it. The former approach (suction) is known as a percutaneous discectomy and is carried out by utilizing hollow needles of special design, which are placed through the back muscles into the center of the disc (into the nucleus area) and then allow suction of the tissue. The latter approach (dissolving) is known as chemonucleolysis, which is carried out by injecting a special enzyme (chymopapain) into the center of the disc. The chemonucleolysis may cause severe pain, spasms, and anaphylactic shock (the mortality rate associated with chemonucleolysis has been estimated at about 0.5%). Both approaches belong to so-called Minimally Invasive Spinal Surgery (hereinafter referred to as MISS) methods. As a result of removal of the disc nucleus tissue, the protruded disc material can then collapse back inside, toward the center of the disc, which can in turn, reduce the pressure on the spine nerve roots.

Many attempts have been made heretofore to improve methods and surgical instruments employed in the percutaneous discectomy procedures.

For example, U.S. Pat. No. 4,545,374 issued in 1985 to R. Jacobson discloses a method and instruments for performing a percutaneous lumbar discectomy. The method consists in accessing the lumbar region of the spinal column by laterally inserting a cannula through the patient's side above the iliac crest to contact a predetermined position in the lumbar region and passing instruments through the cannula. This method is useful for performing percutaneous lumbar discectomy by cutting a portion of the patient's disc annulus and nucleus through the cannula and removing a desired amount of nucleus material. The cannula has a tubular member and anchor means attached to one end of the member for anchoring the cannula in the body tissue to prevent shearing movement between it and the tissue. Other instruments for performing a percutaneous lumbar discectomy are disclosed, including a speculum and trocar for percutaneously inserting the cannula into the patient, a discectomy knife for cutting disc nucleus material and rongeur forceps for removing the disc material. The above instruments may be combined in a surgical apparatus.

The method of U.S. Pat. No. 4,545,374 has the following drawbacks: 1) the material is removed from the center of the disc only, thus preventing a surgeon from excising the fragments from the actual herniation site, which may or may not cause recurrent symptoms; 2) this technique is unsuitable for noncontained (or sequestered) herniations, since it does not give a surgeon access to the epidural space.

U.S. Pat. No. 5,084,043 issued in 1992 to P. Hertzmann et al. describes laser-assisted disc decompression (LDD). It utilizes a high-energy laser beam to vaporize the affected tissue instead of removing it mechanically. Like in the percutaneous approach described above, one of the disadvantages inherent in this procedure is that it deals with the disc nucleus, rather than with the herniation itself.

Several MISS methods, based upon contemporary technology achievements were introduced during last 10–15 years. For instance, U.S. Pat. No. 5,437,661 issued in 1995 to B. Rieser discloses a method for removal of prolapsed nucleus pulposus material on an intervertebral disc by using a laser. A cannula is inserted into the spinal foramen. Once the cannula has passed the ligamentum flavum, a laser fiber is inserted into it. The laser fiber contacts the prolapsed material and a laser beam substantially eliminates the prolapsed material within the spinal foramen.

Lasers are both expensive and somewhat tedious to use in these procedures. Another disadvantage with lasers is the difficulty in judging the depth of tissue ablation. Since the surgeon generally points and shoots the laser without contacting the tissue, he or she does not receive any tactile feedback to know how deeply the laser is cutting. Because healthy tissue, bones, ligaments and spinal nerves lie in the close proximity to the spinal disc, it is essential to maintain a minimum depth of tissue damage, which cannot always be ensured with a laser.

U.S. Pat. No. 6,264,650 issued in 2001 to D. Hovda et al. describes systems, apparatus and methods for ablation, resection, aspiration, collagen shrinkage and/or hemostasis of tissue and other body structures in open and endoscopic spine surgery. In particular, the invention includes a channeling technique in which small holes or channels are formed within spinal discs, and thermal energy is applied to the tissue surface immediately surrounding these holes or channels to cause thermal damage to the tissue surface, thereby stiffening the surrounding tissue structure and reducing the volume of the disc to relieve pressure on the surrounding nerves, and thereby relieving neck or back pain.

U.S. Pat. No. 6,254,553 issued in 2001 to L. Lindgren et al. offers a method and a device for non-invasive treatment of biological tissue by changing or degenerating the tissue. This device has a treatment transducer for treating intervertebral discs, preferably nucleus pulposus, by ultrasound. The ultrasonic field of the ultrasonic transducer is focused in the symptomatic intervertebral disc, preferably in nucleus pulposus of this disc, for heating the tissue to such a temperature that the tissue in the focal area degenerates, whereby the pressure in the intervertebral disc and thus, the pressure against the spinal nerve roots is reduced.

Both methods described in U.S. Pat. No. 6,264,650 and in U.S. Pat. No. 6,254,553 make it complicated for a surgeon to focus treatment on the symptomatic site, without affecting the surrounding tissues.

Single-portal MISS methods are limited to the use of one channel at a time. It was suggested to introduce a second portal to the annulus as described by Shreiber et al. in Clinical Orthopaedics and Related Research No. 238. However, this biportal procedure assumes the second portal to be created from the opposite side to the first portal (bilateral), hence increasing the operating time, post-operative morbidity, surgeon exposure to radiation. It may also cause excessive removal of disc nuclear tissue, therefore increasing the possible post-operative stenosis (narrowing) of the foramen.

Therefore, there is a need for a unilateral multiportal approach for the percutaneous disc procedures. Such attempts were made by either using an oval cannula, which allows using several tools at a time (see U.S. Pat. No. 6,228,022 issued on May 8, 2001 to T. Friesem et al, and U.S. Pat. No. 5,762,629 issued on Jun. 9, 1998 to P. Kambin), or introducing a second cannula for a biportal unilateral approach (the U.S. Pat. No. 5,762,629 and U.S. Pat. No. 5,730,754 issued on Mar. 24, 1998 to T. Obenchain). These approaches do not provide a comprehensive solution for percutaneous disc surgery. Oval cannulae, though providing additional space for instruments, are still too restrictive, while more invasive than circular ones. The method described in U.S. Pat. No. 5,730,754 still needs accurate targeting and it is not sufficiently universal. U.S. Pat. No. 5,762,629 allows inserting a second cannula using a special targeting device, but has following disadvantages: 1) the targeting device is rigid and does not allow the flexibility required by a surgeon for the formation of an angle between inserted cannulae; 2) after cannulae are inserted, the targeting device is removed, leaving the cannulae completely unlinked, so that a surgeon cannot keep them interrelated. In case the position of one of the inserted cannulae should be temporarily changed, it becomes a problem to reorient them, especially when more than two cannulae are used for the surgery.

Another common disadvantage of the existing devices for the percutaneous surgery is that they require the operation to be carried out under X-ray monitoring at all steps of the surgery, i.e., during insertion of each additional cannula and occasionally during the procedure itself. Simultaneously used cannulae are not interrelated with regard to their relative movements, once a cannula is shifted from its original position aligned under X-ray or by means of a special guiding device, it cannot be returned back to the original position, unless X-ray is used again. Such multiple X-ray monitoring subjects both the surgeon and the patient to an increased doze of radiation.

OBJECTS AND SUMMARY OF THE INVENTION

It is an object of the present invention to provide a multiportal device for percutaneous surgery which is simple in construction, reliable and convenient in use, allows insertion of a plurality of cannulae and fixing them relative to each other at a required angle, and permanently maintaining them in controlled positions without resorting to additional X-ray for the duration of the procedure. It is another object to provide the aforementioned device with cannulae having engagement means that allow flexible linking of the distal ends of the cannulae. It is another object to provide a new method for percutaneous spinal surgery based on the use of a multiportal guiding device that allows for simultaneous use of several surgical instruments without the use of additional X-ray targeting at a symptomatic site.

More specifically, a device of the invention for a percutaneous spinal surgery that consists basically of a guide, which during operation is located outside the patient's body, and a link, which during operation is located inside the patient's body. The guiding device is made in the form of a clampable barrel having a central guide opening for insertion a positioning of cannulae and a clamping device for fixing the cannula in a selected position. The barrel has an arched radial arm extending substantially perpendicular to the direction of the aforementioned opening. This arm serves for guiding an auxiliary clamping mechanism which, similarly, to the barrel, has a central opening for insertion and positioning of another cannula and a clamp for fixing the second cannula in a desired position. The arm may have a scale for accurate angular positioning of the second cannula with respect to the first cannula. Since the arm is arched, the cannulae inserted into the guide openings of both barrels will always be automatically aimed at the same point. Thus, once the second barrel is installed onto the guide arm and an a second cannula is inserted into it, no additional X-ray is required for its targeting. If the procedure requires, the clamp of the first barrel can be released and the first barrel can be rotated around a longitudinal axis of the first cannula to another required position and then fixed in a new position, e.g., for subsequent placement of the additional cannula. In other words, the guiding device of the invention allows for multi-dimensional manipulation with one or more cannulae with permanent control of their positions during the cannula placement operations.

The link may consist of a spring-loaded rod installed in one of the cannulae and oriented in the longitudinal direction of this cannula and a loop-like radial projection formed on a spring-loaded rod of the second cannula. Both, the loop and the end of the rod, that engages this loop, are located on the distal ends of both cannulae in cutoffs formed in the sidewalls of the respective cannulae. Engagement of the end of the rod of one cannula with the loop of the second cannula keeps the distal ends of both cannulae, which during the surgery are located inside the patient's body, linked together, while allowing them to be angularly and linearly moved without disconnection.

A percutaneous surgical disc procedure with the use of the device of the invention is carried out by percutaneously entering the patient's back in the posterolateral direction with one cannula until it approaches the vertebral foramen next to the disc herniation to be removed; percutaneously enter the second cannula through the second guide barrel of the guide device at an angle to the first cannula defined by the surgeon; linking both cannulae at their distal ends by means of the inner link mechanism loosely enough to allow independent cannulae movement, though to be able to get their distal ends to get back together if needed; removing the auxiliary clamping mechanism from the second cannula; and using the guide in the same manner as above for inserting a third cannula and linking it to the first cannula at the distal ends in the same way it was done with the second cannula; and removing the guide.

The present invention allows performing a surgery using all inserted cannulae simultaneously, in the way a surgeon may need it (site visualization, tissue retraction, material removal, etc.). The method also assumes the procedure for unlinking the cannulae after the surgery is done and prior to the removal of the cannulae from the patient's body.

The method of the invention requires only small incision for every inserted cannula, provides a unilateral multiportal approach that allows a physician to increase safety of surgery by performing it with a continuous visual control and with all necessary instrumentation simultaneously being in place. As a regular percutaneous method, this approach requires local anesthesia, thus avoiding the risk, which might be caused in the case of general anesthesia.

DETAILED DESCRIPTION OF A PREFERRED EMBODIMENT

Figure 5:
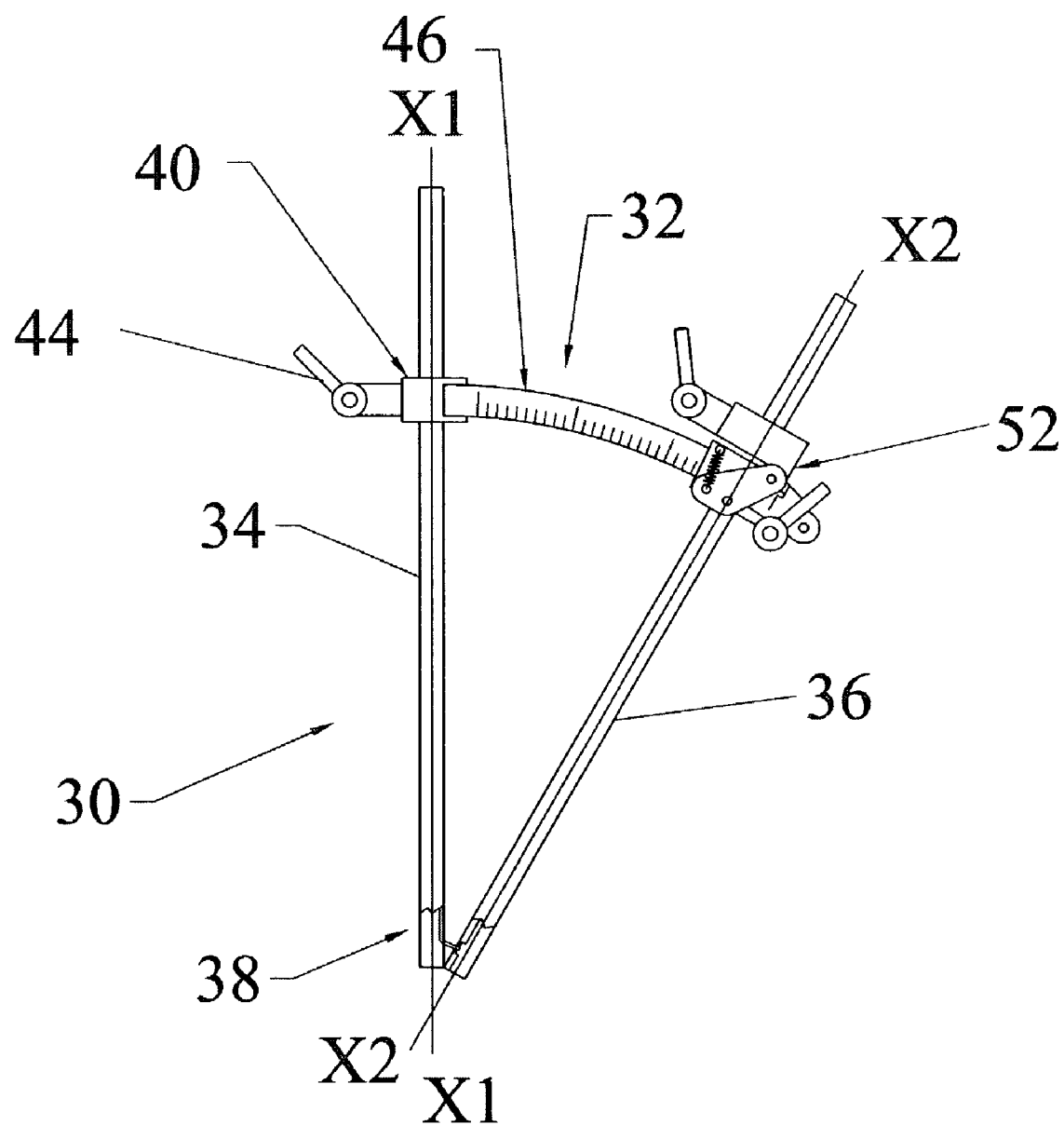
FIG. 5 is a general side view of a guiding device of the invention with cannulae inserted for use in percutaneous spinal surgery.
Figure 6:
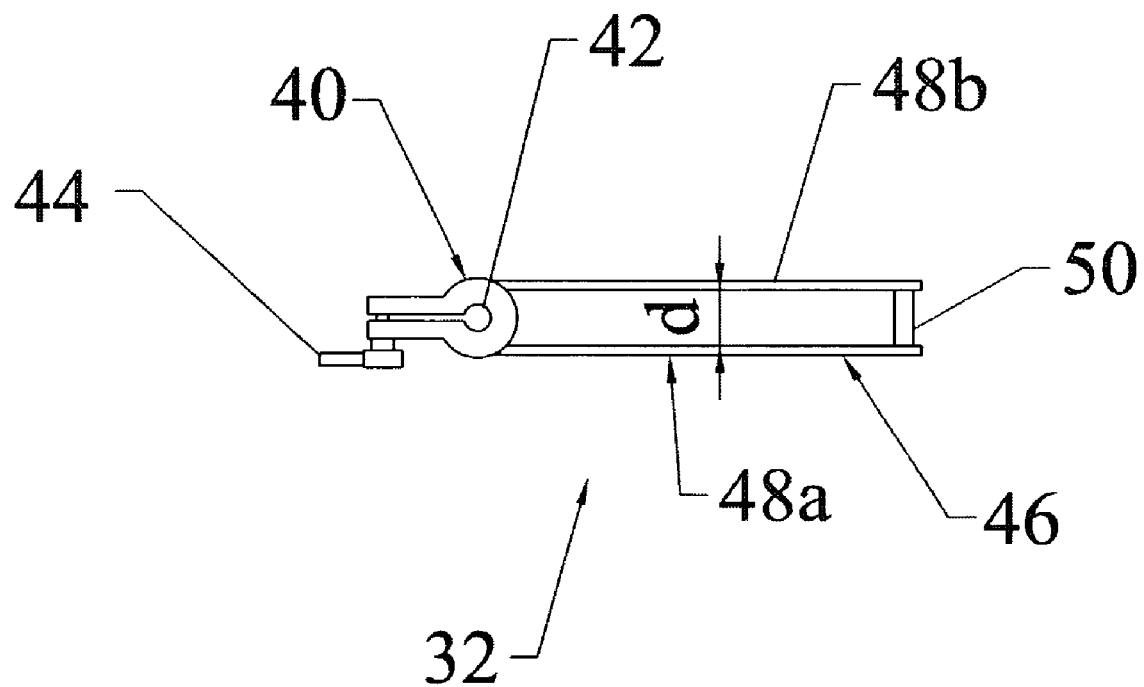
FIG. 6 is a top view on a first guide barrel with an arm (the auxiliary clamping mechanism and cannulae are not shown).

A general side view of the device of the invention with cannulae inserted for use in percutaneous spinal surgery is shown in FIG. 5. FIG. 6 is a top view on a first cannula first guiding unit made, e.g., in the form of a guide barrel (hereinafter referred to simply as "barrel") with an arm (the auxiliary clamping mechanism and cannulae are not shown). As shown in this drawing, the device, which in general is designated by reference numeral 30, consists of an guiding device 32 for insertion, positioning, and fixation of cannulae 34 and 36 (only two cannulae are shown in FIG. 5, although more than two can be used, if necessary) and a linking mechanism 38 provided in the cannulae 34 and 36 for interconnection of the distal ends of these cannulae when they are inserted into the patient's body (not shown) for surgery.

More specifically, the guiding device 32, which during operation is located outside the patient's body, is made in the form of a clampable barrel 40 having a central guide opening 42 shown in FIG. 6 for insertion an positioning of the cannula 34 (FIG. 5) and a clamping device 44 for fixing the cannula 34 in a selected position in the axial direction of the cannula 34 shown by axis $X_1$—$X_1$. In the embodiment shown in FIGS. 5 and 6, the mechanism 44 for clamping the first cannula 34 is made in the form of a C-shaped clamp tightened by means of a wing-head screw.

The barrel 40 has an arched radial arm 46 extending substantially perpendicular to the direction of the aforementioned axis $X_1$—$X_1$. This arm 46 can be rigidly connected to the barrel 40 or made integrally therewith. As shown in FIG. 6, the radial arm consists of two elongated parallel arch-shaped plates 48a and 48b with a spacer 50 between the plates 48a and 48b at the free end of the arm 46. The width d between the plates should be sufficient at least for insertion of the second cannula 36 (FIG. 5).

Figure 7:
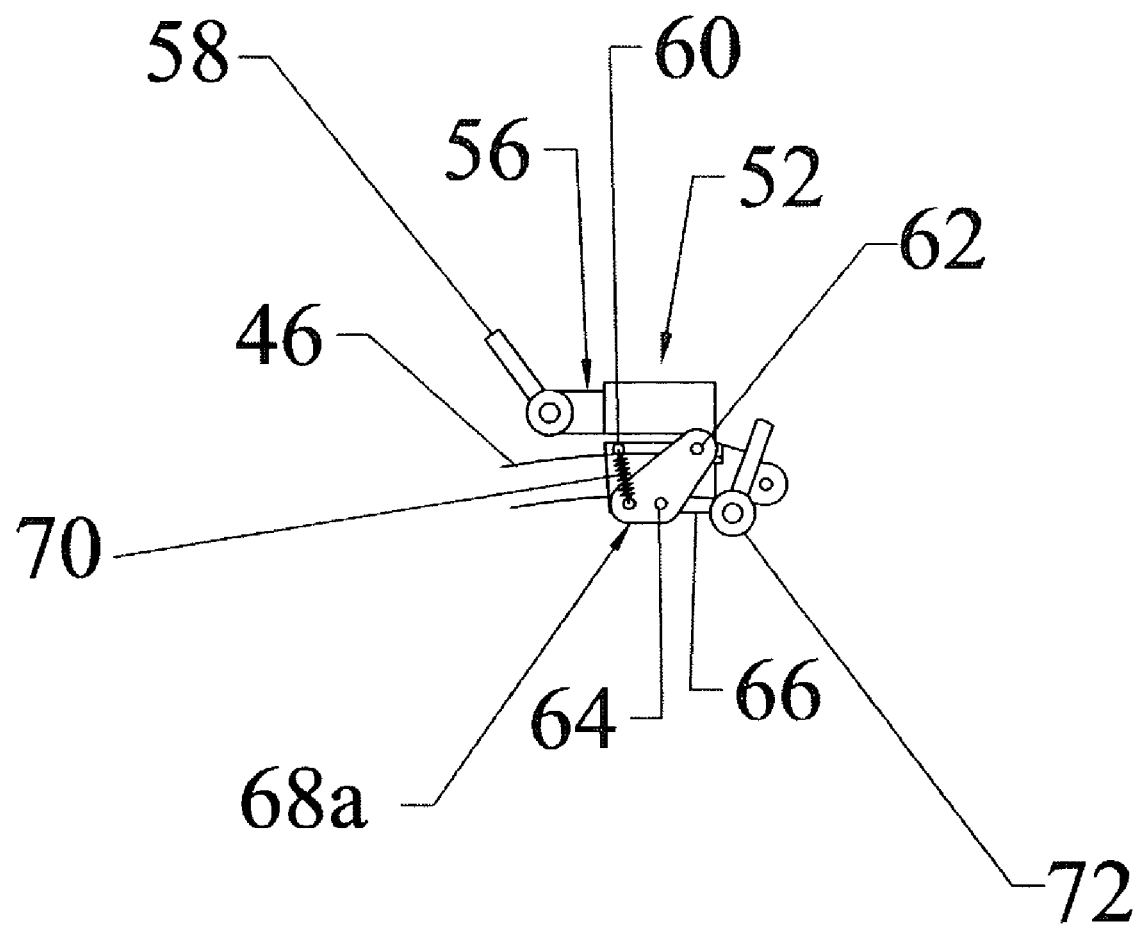
FIG. 7 is a side view on an auxiliary clamping mechanism for mounting on the radial arm of the guiding device.

The arm 46 serves for guiding an auxiliary cannula guiding and clamping mechanism 52 (hereinafter referred to as an auxiliary clamping mechanism), which is shown in FIG. 7 (side view) and FIG. 8 (top view). The clamping mechanism 52 consists of a C-shaped clamping device 56 located above the arm 46 and a carriage 66 which supports the clamping mechanism 52 and rides along the arm 46. Similarly to the barrel 40, the mechanism 52 has a central opening 54 for insertion and positioning of another cannula 36 and a clamping lever 58. In order to provide a gap-free riding of the auxiliary clamping mechanism 52 along the arm 46, the carriage 66 has two pairs of guide rollers 60 and 62 (only one roller of each pair is shown in FIG. 7) rotationally installed on the upper side of the carriage 66 for rolling along the upper edges of the plates 48*a* and 48*b* that forms the arm 46 (see FIG. 6). Another pair of rollers 64 (only one of which is seen in FIG. 7) is rotationally installed on the lower part of the carriage 66 for rolling along the lower edges of the plates 48*a* and 48*b*.

Figure 8:
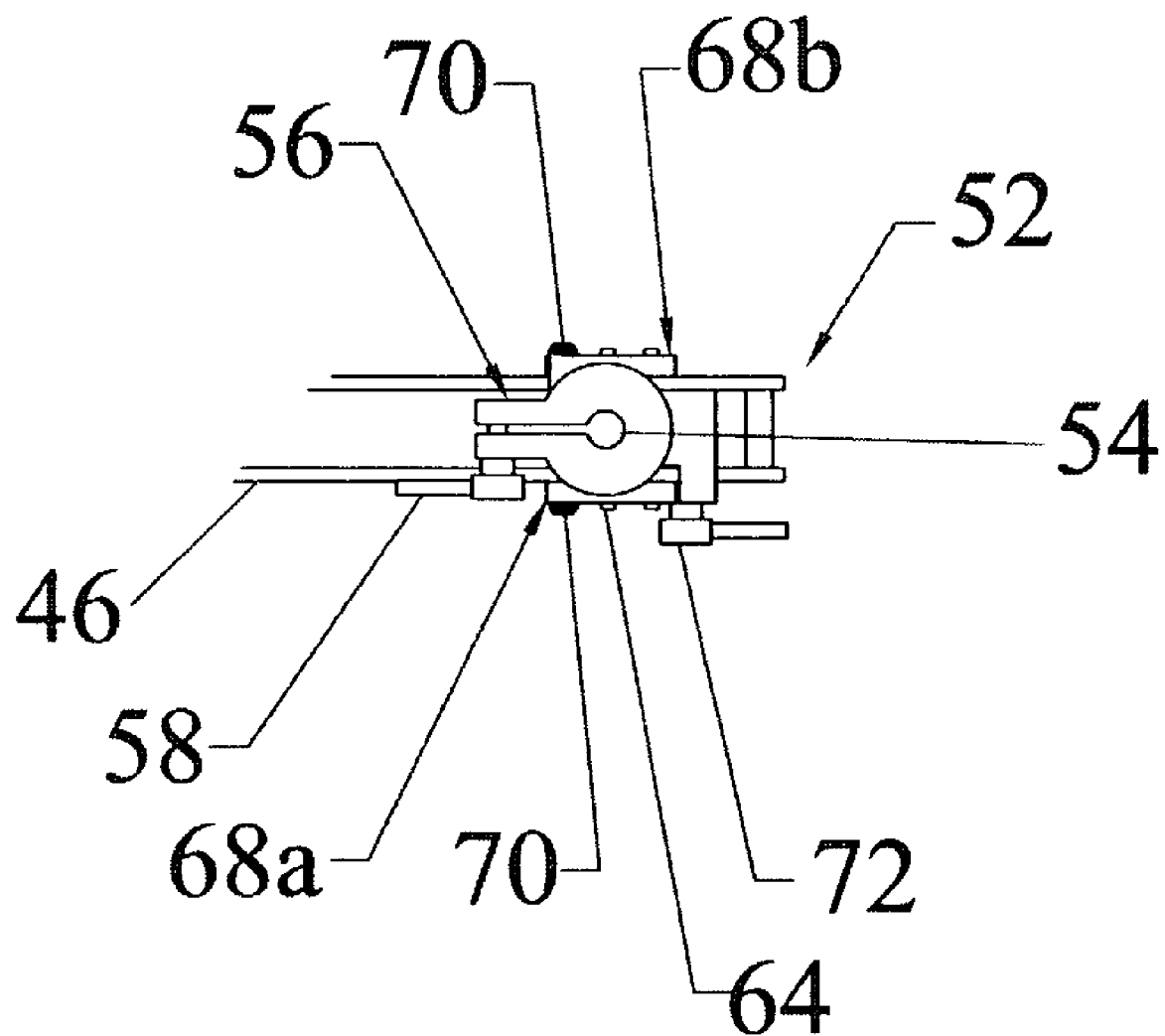
FIG. 8 is a top view of the clamping mechanism of FIG. 7.

In order to provide constant gap-free contact of the rollers 60, 62, and 64 with the guiding surfaces of the arm 46, the auxiliary clamping mechanism 52 is provided with a pair of eccentric levers 68*a* and 68*b* (FIGS. 7 and 8). These levers are rotationally supported by the axes of the rollers 62 and support the aforementioned rollers 64. A pair of springs 70 (only one of which is seen in FIG. 7) constantly urges the levers 68*a* and 68*b* in the direction that maintains the rollers in constant gap-free contact with the arm 46.

It is understood that the auxiliary clamping mechanism 52 can be moved along the arm 46. In order to fix this mechanism in selected position, the carriage 66 has a screw-type clamp 72 for fixing the carriage, along with the C-shaped clamping mechanism 52, on the arm 46.

Thus, it is understood that the guiding device 32 shown and described in connection with FIGS. 5 through 8 makes it possible for a physician to accurately manipulate, with the cannulae at the time of their installation and during the procedure.

One of essential distinguishing features of the device and method of the present invention is a provision of a linking device 38 that is located on the distal ends of the cannulae 34 and 36 inserted into the patient's body and intended for maintaining the distal ends of the aforementioned cannulae in interrelated positions.

A specific example of the linking device 38 suitable for the purposes of the present invention is shown in FIGS. 9 through 14. It is understood that this specific embodiment is shown in one of simplified forms for understanding the principle of operation of such a device and is given only as an example that should not be construed as limiting the scope of the invention.

Figure 9:
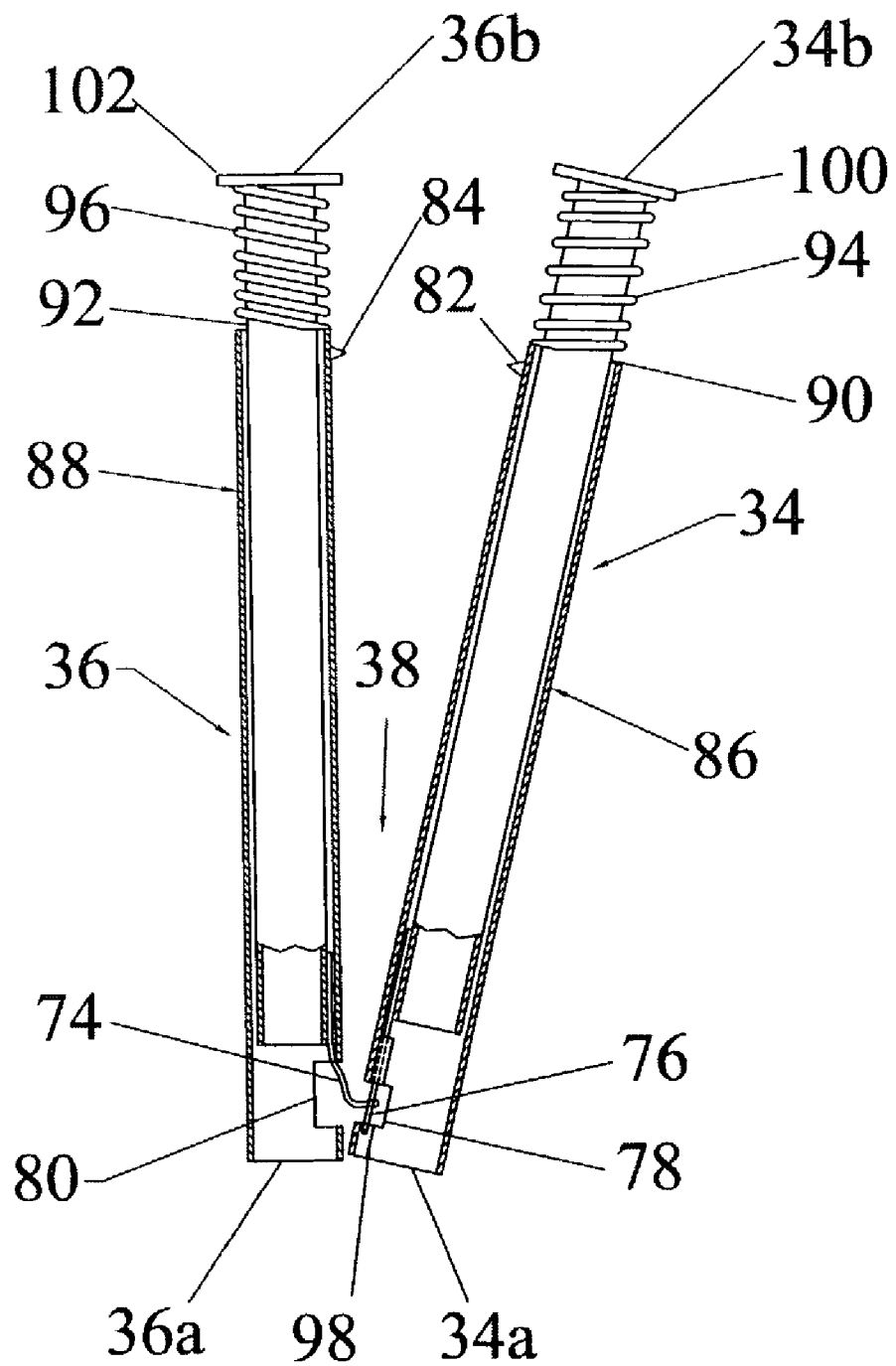
FIG. 9 is a side view of two cannulae with their distal ends locked together.

More specifically, the linking device 38 consists of two engaging members 74 and 76, which are shown in an engaged state in FIG. 9 which is a side view of both cannulae 34 and 36 with their distal ends locked together. Parts of the distal ends of the cannulae 34 and 36 are removed for revealing the engaged elements. For illustration purposes the cannulae 34 and 36 are shown in FIG. 9 outside the patient's body, although the condition shown in FIG. 9 is more typical for the surgery procedure.

In order to implement the linking device 38, each cannula (34 and 36) should have a respective opening 78 (in cannula 34) and 80 (in cannula 36). These openings are formed close to the distal ends 34*a* and 36*a*, respectively. When the distal ends of the cannulae 34 and 36 are inserted into the patient's body, the aforementioned openings 78 and 80 are not seen. In order to orient them so that they face each other, special marks 82 and 84, which are conventionally shown in FIG. 9 as small projections, can be provided on the surfaces of the cannulae close to their respective ends 34*b* and 36*b*.

As shown in FIG. 9, each cannula 34 and 36 consists of an external tubular body 86 and 88, respectively, and an internal tubular body 90 and 92, respectively, which is telescopically inserted into the respective external tubular body and is urged by a respective spring 94 and 96 in an appropriate manner. Each spring 94 and 96 is held in place between the proximal edge of the respective external tubular body 86 and 88 and a stopper 100 and 102 on the proximal end of the respective internal tubular body 90 and 92.

Figure 10:
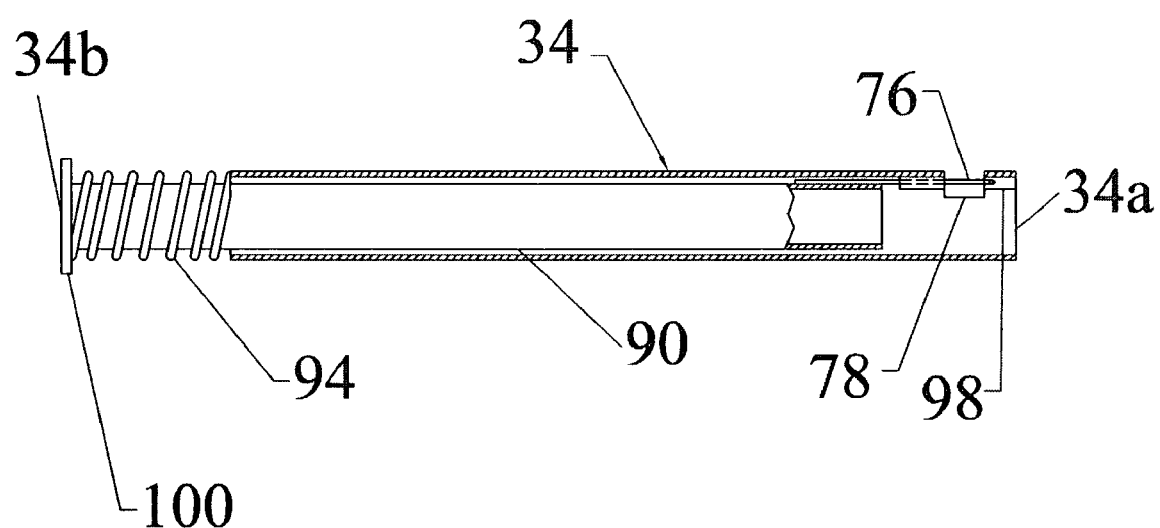
FIG. 10 is a longitudinal sectional view of the central cannula with the longitudinal rod inside this cannula.

As shown in FIG. 10, which is a longitudinal sectional view of the cannula 34, the engaging member 76 is made in the form of an elongated rod, which is rigidly connected to the internal tubular body 90 and is constantly urged by a spring 94 located on the proximal end of the cannula 34 towards the distal end 34*a* so that in its normal state the distal end of the rod 76 overlaps the opening 78 (FIG. 10). In order to prevent engagement of the locking elements with the surgical instruments that will be inserted into the cannula, the distal ends of the cannula 34 has on its inner wall a protective guard 98.

Figure 11:
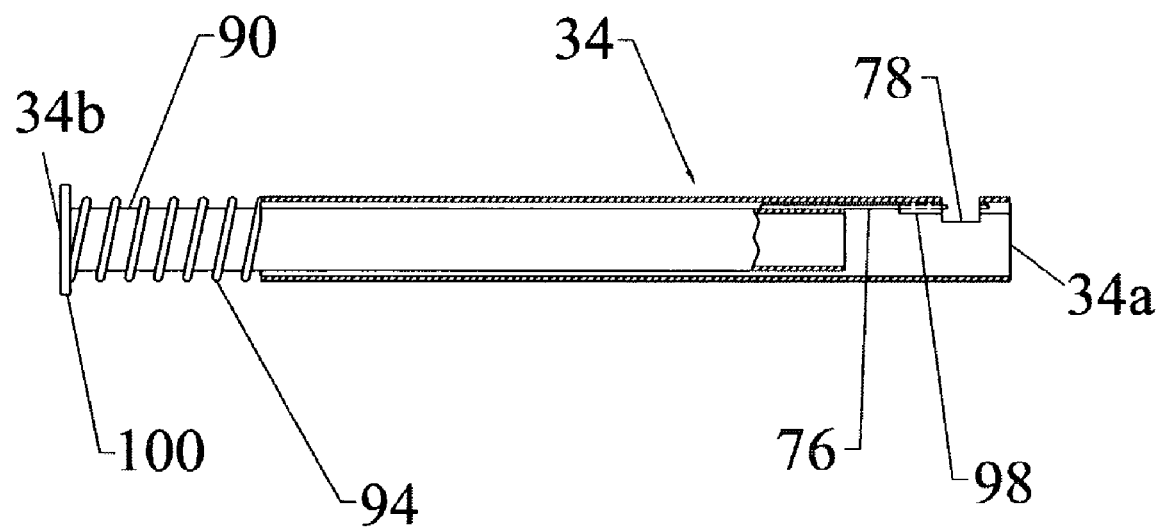
FIG. 11 is a view similar to the view of FIG. 10 but with the internal tubular body pulled over towards the proximal end of the cannula.

FIG. 11 is a view similar to the view of FIG. 10 but with the internal tubular body 90 pulled over towards the proximal end of the cannula 34*b* with an external force so that the distal end of the rod 76 is raised above the opening 78.

Figure 12A:
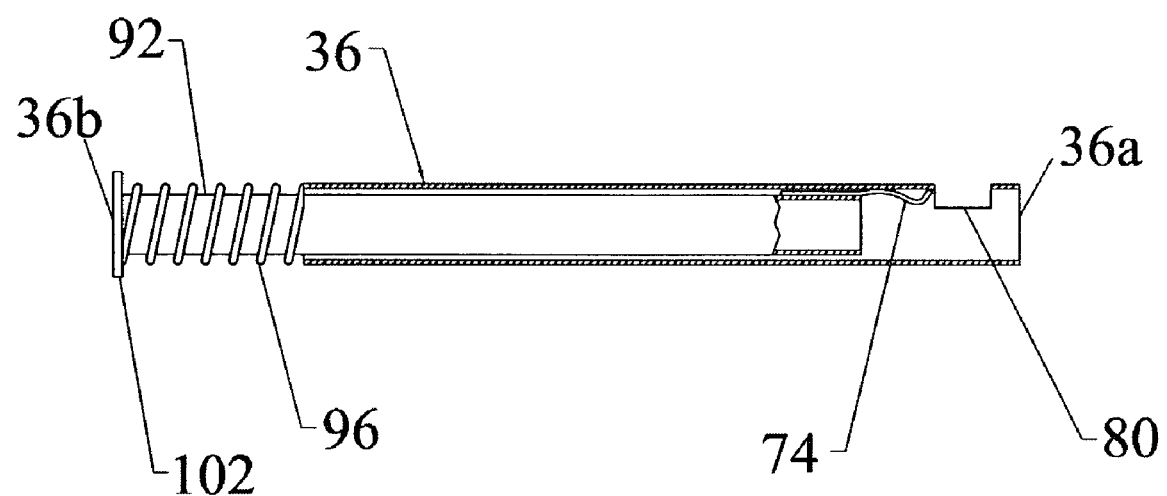
FIG. 12A is a longitudinal sectional view of the side cannula with the loop-like hook inside this cannula for engagement with the rod of the central cannula.

As shown in FIG. 12A, which is a longitudinal sectional view of the cannula 36, the engaging member 74 is made in the form of a hooked loop on the distal end of the internal tubular body 92, which is constantly urged by a spring 96 located on the proximal end of the cannula 36 towards the proximal end 36*b* so that in its normal state the loop 74 is maintained above the opening 80. The shape of the loop 74 is shown in FIG. 14, which is a fragmental view of the distal end of the cannula 36 in the direction of arrow A of FIG. 13A and with the loop pushed down by pressing on the stopper 102.

Figure 12B:
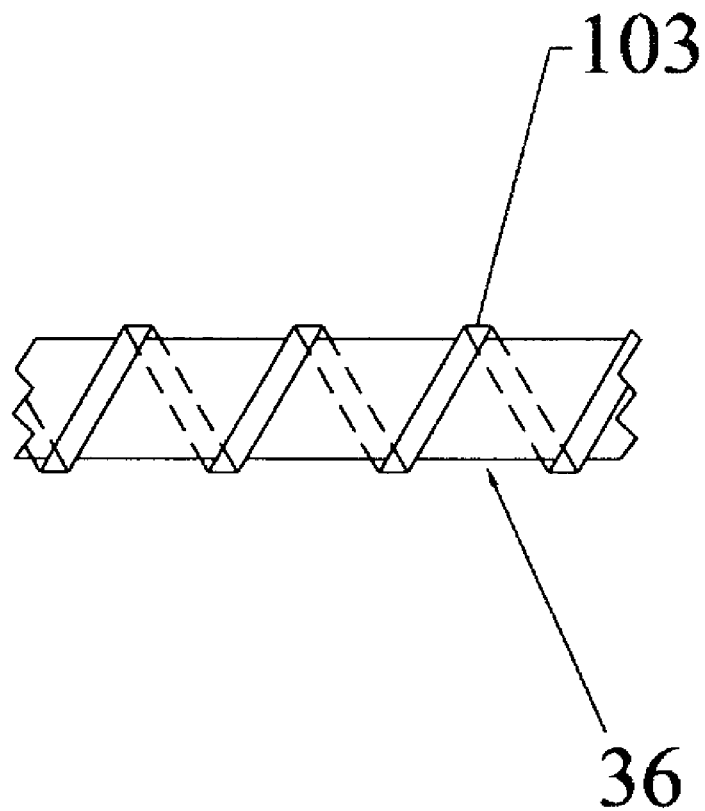
FIG. 12B is a side view on a part of a cannula having a helical projection on its external surface.

As shown in FIG. 12B, which is a side view on a part of the cannula 36, it may be provided with an external helical projection 103 that improves stability of the cannula in the incision. It is understood that the helical projection 103 should have very smooth and rounded edges in order not to damage the surrounding body tissue. It is also understood that the same projection can be formed on the external surface of other cannulae.

Figure 13A:
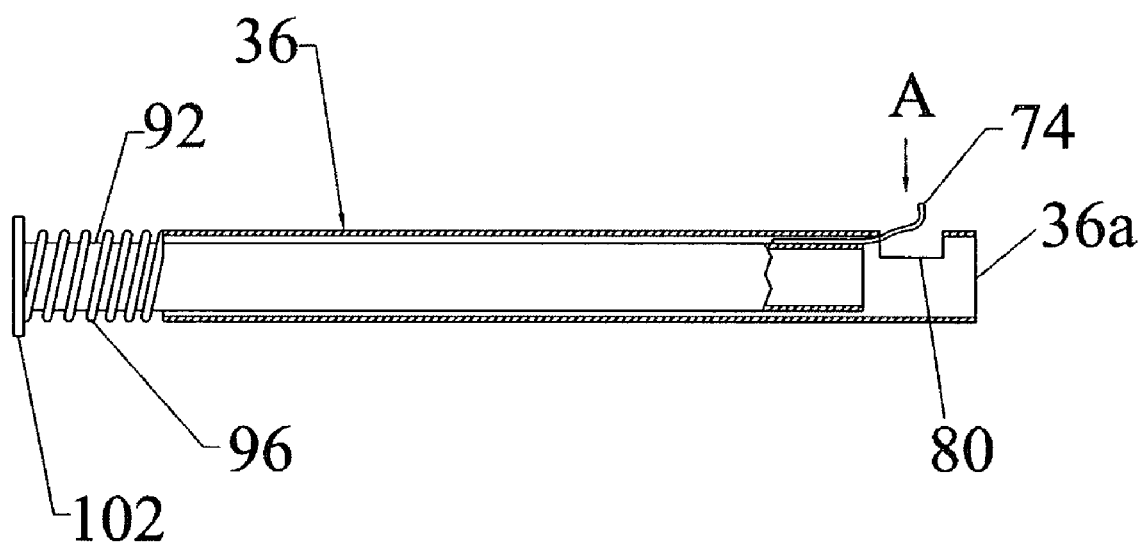
FIG. 13A is a view similar to the view of FIG. 12A but with the internal tubular body pushed down towards the distal end of the side cannula.
Figure 14:
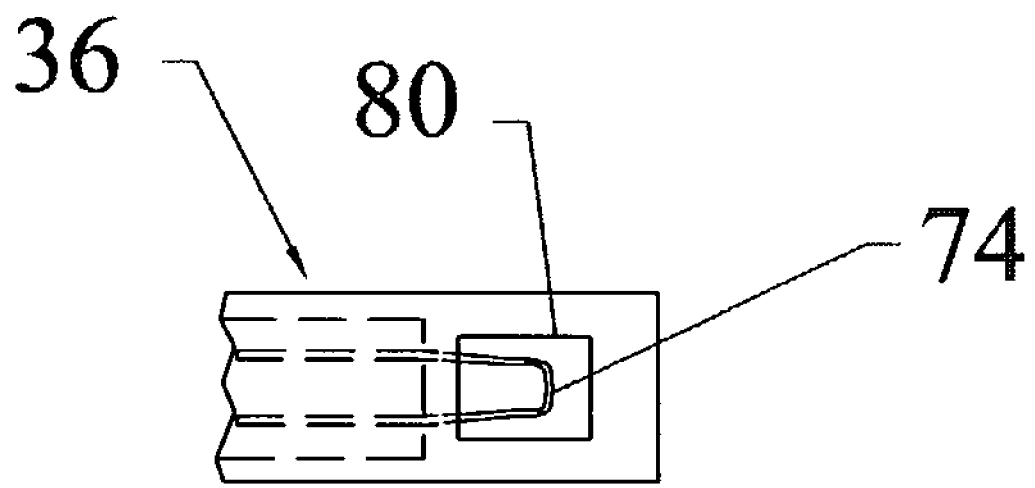
FIG. 14 is a fragmental view of the distal end of the side cannula in the direction of arrow A of FIG. 13A and with the loop pushed down.

FIG. 13A is a view similar to the view of FIG. 12A but with the internal tubular body 92 pushed down towards the distal end 36*a* of the cannula 36 with an external force so that the distal end of the loop 74 enters the opening 80 and protrudes radially outwardly from the cannula 36, as shown in FIGS. 13A and 14.

Figure 13B:
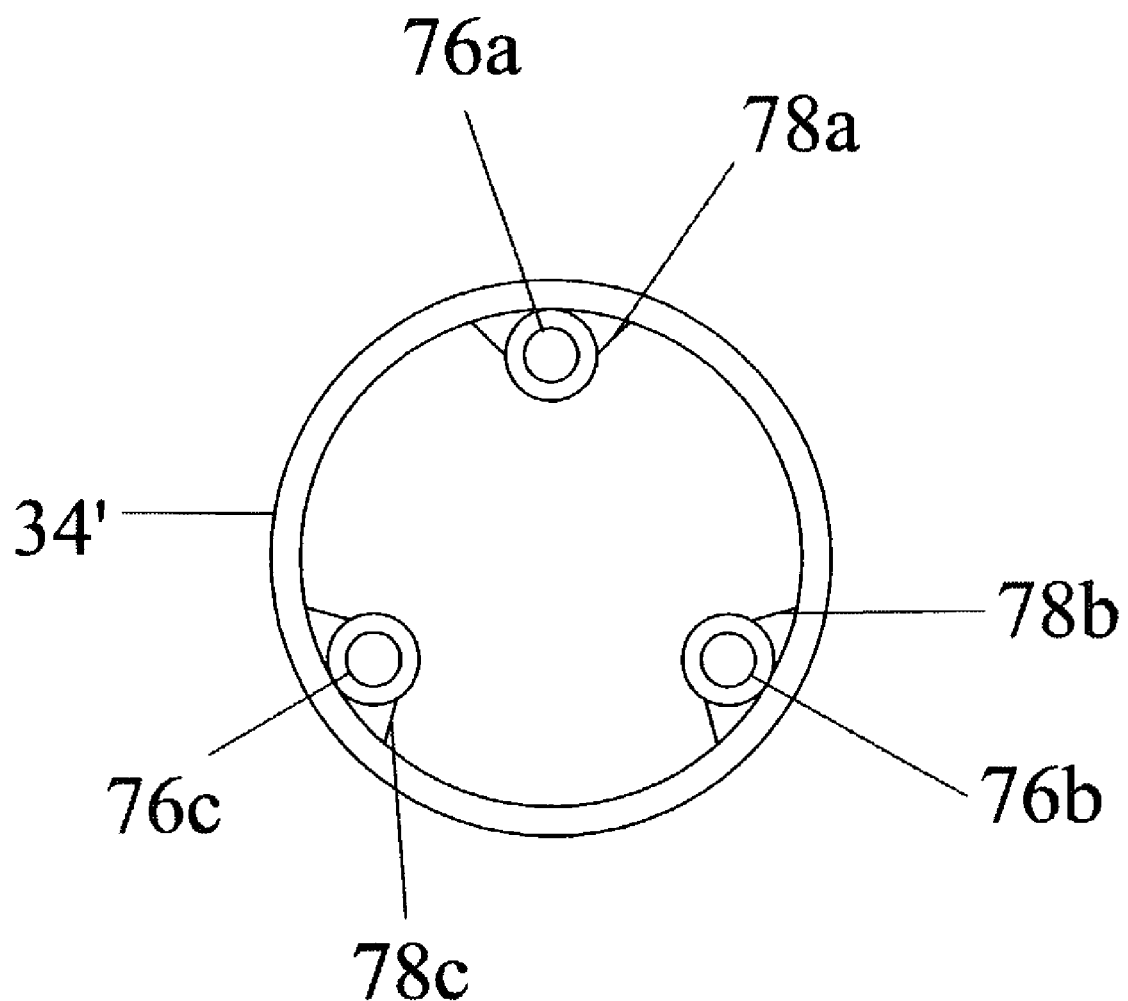
FIG. 13B is a sectional view of the central cannula with three windows on the distal end of the cannula and with three respective locking rods.

If necessary, the distal end of the cannula 34 may have more than one window 78 and more than one rod 76 aligned with a respective window. This is shown in FIG. 13B which is a cross-sectional view of a cannula 34' with three windows 78*a*, 78*b*, and 78*c* and with three respective rods 76*a*, 76*b*, and 76*c*.

The multiportal device 30 for percutaneous surgery made in accordance with the embodiment of the invention shown and described with reference to FIGS. 5 through 14 operates in the following manner.

Figure 1:
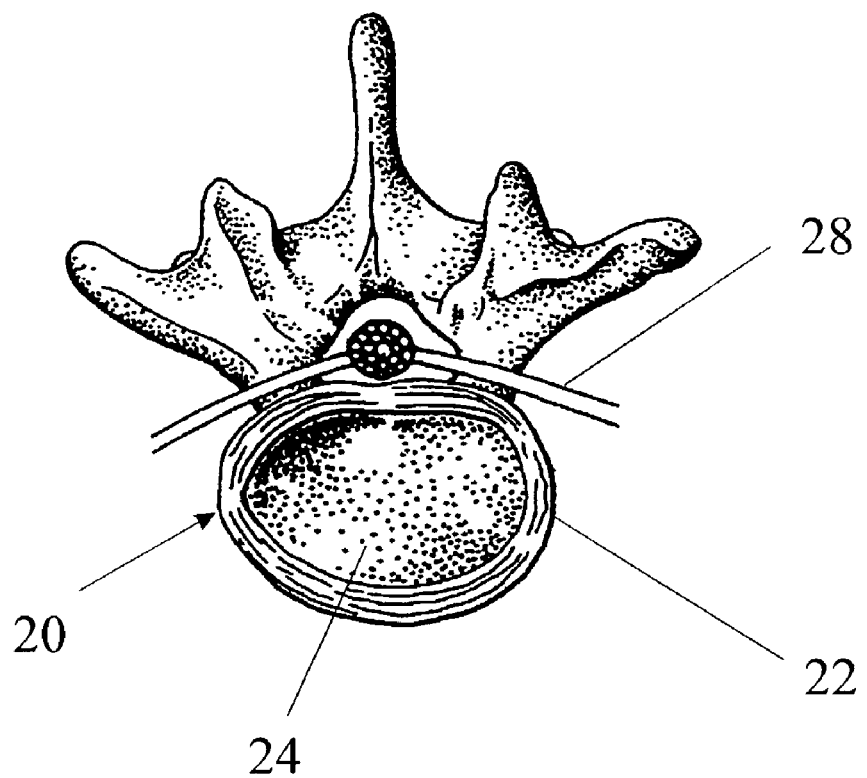
FIG. 1 is a cross-sectional view of a vertebral column through a healthy intervertebral disc.
Figure 2:
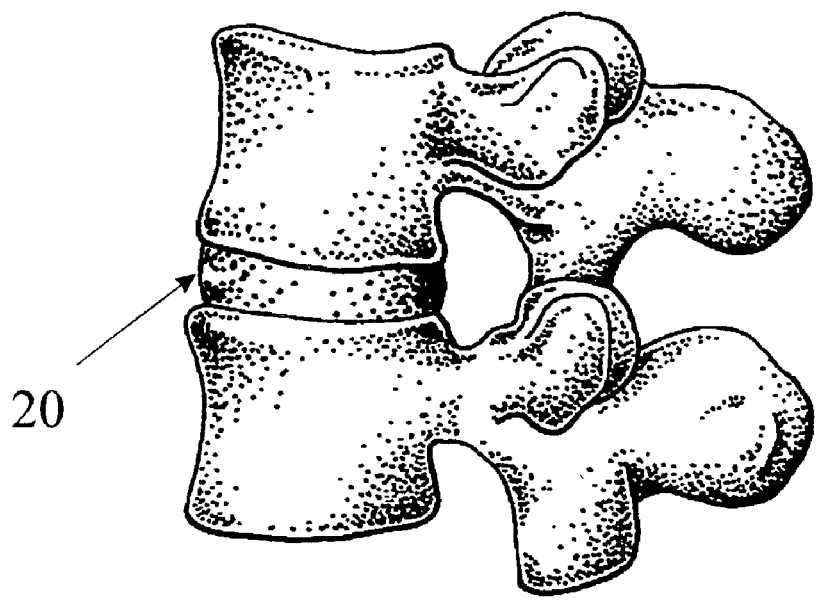
FIG. 2 is a side view on a part of the vertebral column illustrating the position of the disc of FIG. 1.
Figure 3:
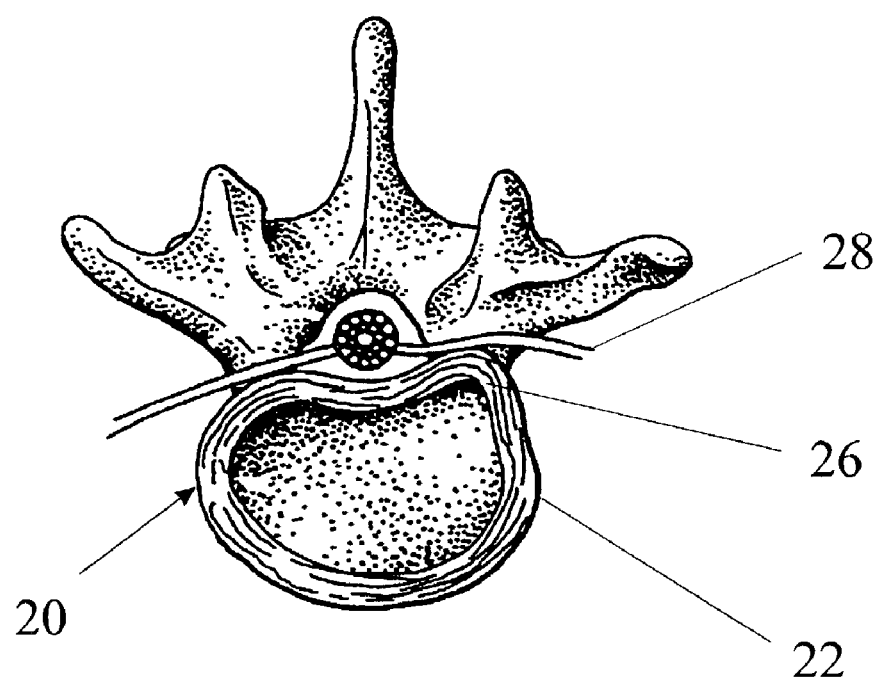
FIG. 3 is a view similar to FIG. 1 illustrating a herniated disc that might require an operation.
Figure 4:
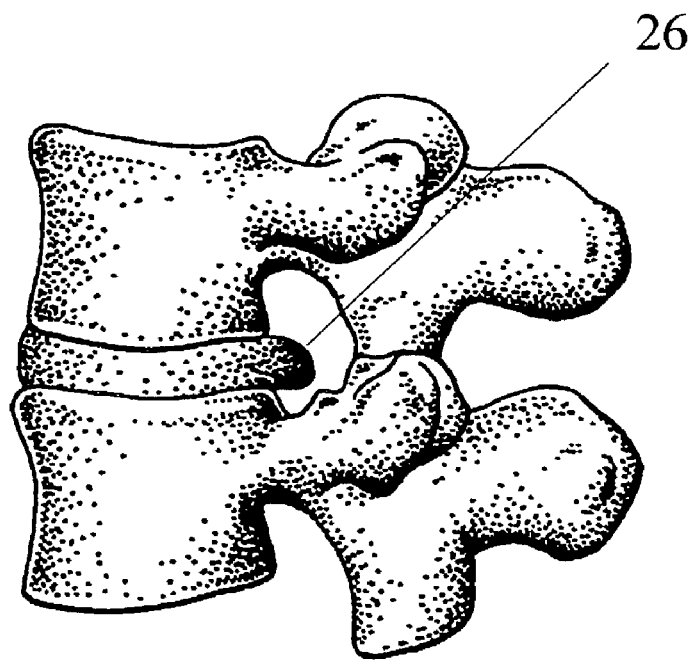
FIG. 4 is a side view similar to FIG. 2 illustrating a herniated disc protruded into the foramen.
Figure 15:
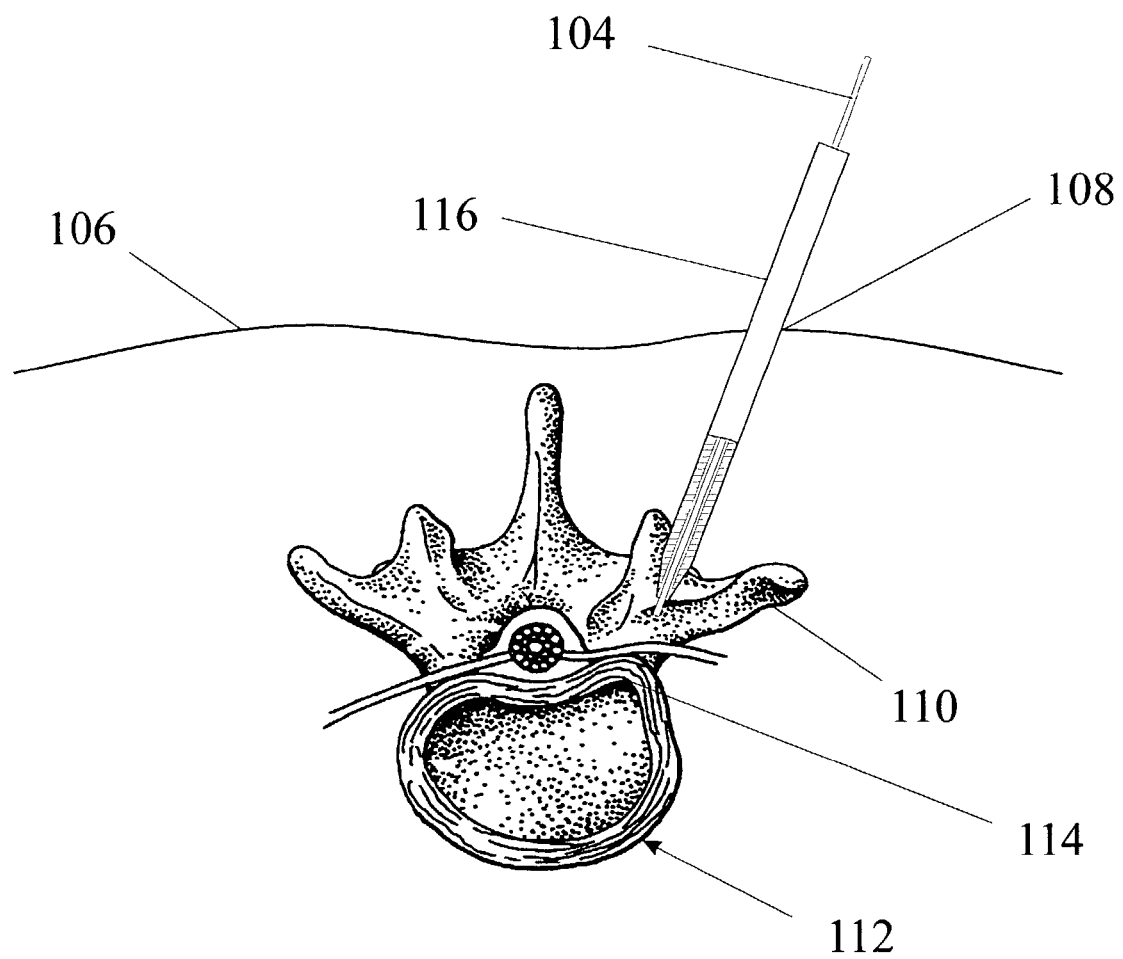
FIG. 15 is a schematic sectional view illustrating position of a guide wire and the obturator inserted into the patient's body in the initial stage of the surgery.

After being diagnosed as having a prolapsed disc causing a nerve root impingement of the type shown in FIGS. 3 and 4, the patient is positioned on a radiolucent table (not shown) in a prone position. First, a surgeon inserts a special needle, which usually has a bore. A needle is rigid enough to stay straight and helps surgeon to get to a desired position inside the patient's body under the fluoroscopic guidance. A guidewire 104 (FIG. 15) made of suitable stainless steel, of about 1.0 to 1.25 mm in diameter is advanced through the needle through the skin 106 of the patient's back at a predefined entry point 108 posterolaterally under the fluoroscopic observation. The guidewire 104 is advanced till it reaches the target position specified by a surgeon, usually at the foramen of the vertebra 110 next to a symptomatic intervertebral disc 112, close to the herniation 114. After the guidewire 104 is in the position, the needle is removed from the patient's, and a surgeon does an incision around the entry point 108 in order to be able to insert the next tools.

At this point, a cannulated obturator 116 (FIG. 15) with a lumen, diameter of which is slightly larger than the diameter of the guidewire 104, is passed over the guidewire 104 through the patient's skin 106 until the distal end of the obturator 116 reaches the same position as the guidewire 104. At this step guidewire 104 may or may not be removed.

Figure 16:
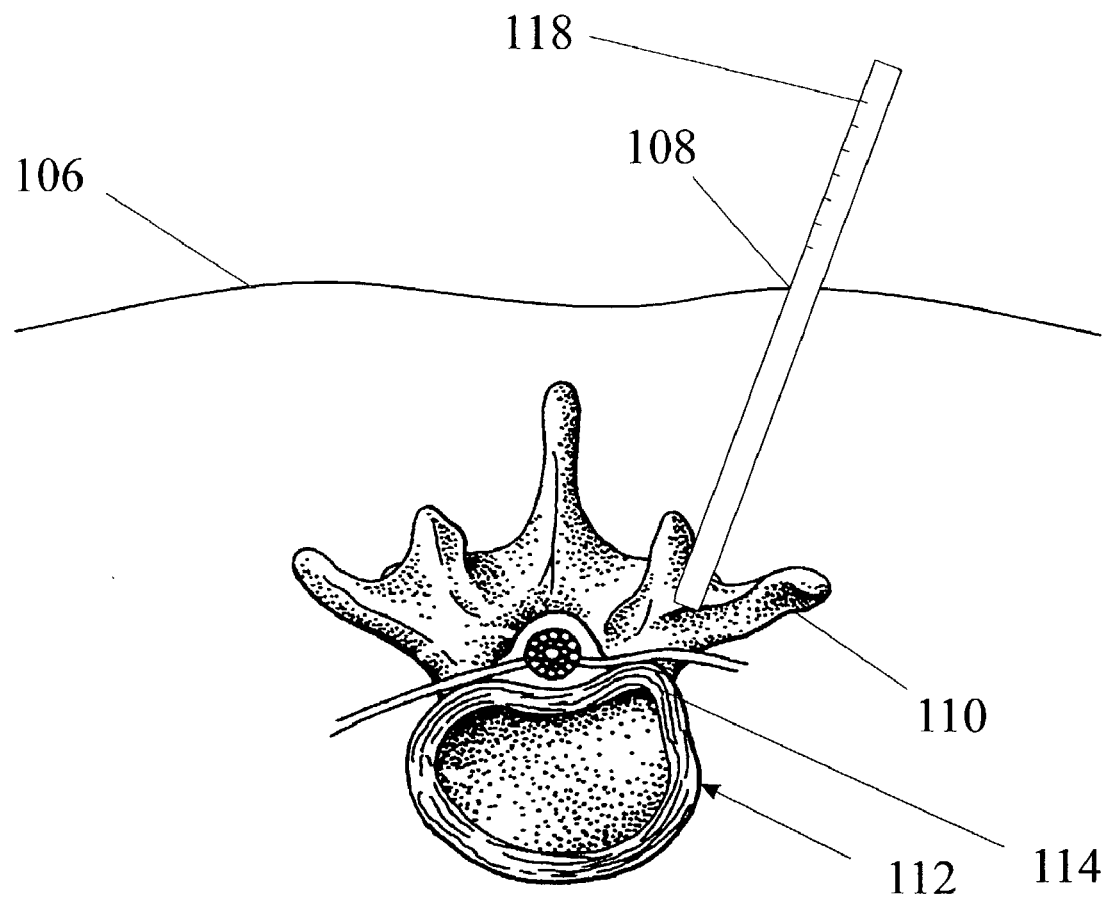
FIG. 16 is a view similar to FIG. 15 illustrating position of the cannula after insertion into the patient's body.

The cannula 34, that may have an outer diameter of about 4–7 mm with external gradations 118 on its surface is then advanced over the obturator 116 till the distal end of the cannula 34 reaches the position of the distal end of the obturator 116. At this point, both the obturator 116 and the guidewire 104 (if it has still not been removed) are removed. The position of the cannula 34 inserted into the patient's body and with the obturator 116 and the guidewire 104 removed is shown in FIG. 16.

In order to obviate extraneous drawings, the following description of the procedure will be made with reference to FIGS. 5 through 14, assuming that the cannulae 34 and 36 have been inserted into the patient's body, even though the body is not shown in the aforementioned drawings. Thus, let us assume, with reference to FIG. 5, that only the cannula 34 is inserted in place required for the operation.

Now, the guiding device 32 is advanced over the proximal end 34b of the cannula 34 by fitting the opening 42 (FIG. 6) onto the proximal end 34b of the cannula 34. The barrel 40 of the guiding device 32 is shifted down along the cannula 34 to a required position determined by means of the scale 118. The barrel 40 is secured in the selected position by means of the clamping device 44. At this point, the fluoroscopic equipment (not shown) might be turned off.

The auxiliary clamping mechanism 52, which is always supported on the arm 46 (FIG. 7) is then unlocked using the clamp 72 and moved over the arm 46 until the angle between the longitudinal axis $X_1$—$X_1$ of the cannula 34 and the longitudinal axis $X_2$—$X_2$ of the opening 54 (FIG. 8) of the auxiliary clamping mechanism becomes suitable for the procedure. The auxiliary clamping mechanism 52 is then locked on the arm 46 with the clamp 72.

The second cannula 36 with the trocar (not shown in the drawings) is then advanced through the opening 54 in the auxiliary clamping mechanism 52. Using the clamp 58, the size of the opening 54 is tightened for clamping the cannula 36. The cannula with the trocar is advanced through the skin (not shown in FIG. 5) with an incision made in advance and then through the soft tissues of the patient until the second cannula 36 reaches its position. Since the arm 46 is arched, the distal ends 34a and 36a of both cannulae come to the same position, defined by the radius of that arch, as shown in FIG. 5.

The guiding device 70 now may be removed from the second cannula 50a at this point and used again in the same way to insert the next cannula 50b, if necessary (FIG. 6).

Once the distal ends of the cannulae 34 and 36 are in place, the surgeon may interlock these ends by means of the linking device 38. First, both cannulae 34 and 36 are rotated around their respective longitudinal axes $X_1$—$X_1$ and $X_2$—$X_2$ for alignment of the marks 82 and 84 in positions facing each other. Thus, the openings 78 and 80 in the sidewalls on the distal ends of the cannulae 34 and 36 are automatically located against each other.

In order to percutaneously engage the distal ends of the cannulae 34 and 36, the internal tubular body 90 of the cannula 34 is pulled up, so that the distal end of the rod 76 is raised above the opening 78. Thereafter, the internal tubular body 92 of the cannula 36 is pushed down so that the hooked-like loop 74 protrudes radially outwardly from the opening 80 and enters the opening 78 of the cannula 34. The raised rod 76 is released and penetrates into the loop 76 thus interlocking the cannulae together. The interlocking position of the cannulae shown in FIG. 9 will be maintained after both internal tubular bodies are released. Due to resilient properties of the loop 74, in the position of the cannulae shown in FIG. 9 with the loop portion 74 engaged with the end of the rod 76, the cannulae 34 and 36 can be pivoted around the point of the connection with three reasonably limited degrees of freedom, i.e., in the axial direction of the cannulae (for the cannula 36) and with two degrees of freedom for both cannulae (rotation within a solid angle with the fulcrum in the point of connection).

Now the guiding device 32 can be removed or used for disconnection of the second cannula 36 and for connection of the third cannula, after the arm 46 is turned to an appropriate position in the direction perpendicular to the plane of the drawing of FIG. 5. Now the surgery can be performed by utilizing all inserted cannulae and by using any surgical instruments into the cannulae with a freedom of manipulation provided by the linking device 38.

For disconnection of the linked cannulae 34 and 36 after completion of the surgery, the internal tubular body 90 of the cannula 34 is pulled up until the distal end of the rod 76 is removed from the loop 74, which will automatically move up to its normal position shown in FIG. 12 under the action of the spring 96.

Thus, it has been shown that the present invention provides a multiportal device for percutaneous surgery which is simple in construction, reliable and convenient in use, allows insertion of a plurality of cannulae and fixing them relative to each other at a required angle, and permanently maintaining them in controlled positions without resorting to additional X-ray. The device of the invention has engagement means that allow flexible linking of the distal ends of the cannulae. The invention also provides a new method for percutaneous spinal surgery based on the use of a multiportal guiding device that allows for simultaneous use of several surgical instruments without the use of additional X-ray targeting at a symptomatic site.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For example, three or more cannulae can be linked by the guiding device and used simultaneously. The guiding device may have several freely rotating guiding barrels with respective radial arms. The cannulae may have a non-circular cross section. The alignment marks can be made in the form of grooves, projections, or color stripes. The linking mechanism was shown in the form of a loop-like hook and a rod only as an example and can be embodied in any other form. The stabilizing means on the outer surface of the cannula may be made in a form different from a helical projection, e.g., in the form of concentric ribs or grooves.

What is claimed is:

1. A multiportal device for percutaneous surgery at a symptomatic site, comprising:
   a cannula-guiding device;
   a first cannula for percutaneous access to said symptomatic site and at least a second cannula for percutaneous access to said symptomatic site, said first cannula having a proximal end and a distal end, said at least a second cannula having a proximal end a distal end;

a cannula-linking mechanism with means for pivotally connecting said distal end of said first cannula with said distal end of said at least a second cannula, allowing relative motion of said first cannula and said at least a second cannula;

a first guiding unit, which has a first longitudinal axis with a first through opening in the direction of said first longitudinal axis for insertion of said first cannula and at least one arm radially projecting from said first guiding unit in a direction substantially perpendicular to said first longitudinal axis of said first guiding unit;

a second guiding unit, which has a second longitudinal axis with a second through opening in the direction of said second longitudinal axis for insertion of said at least a second cannula, said second guiding unit having means for riding along said at least one arm;

a first clamping mechanism for clamping a cannula, selected from a group of cannulae, consisting of said first cannula and said at least a second cannula, said first clamping mechanism being located on a guiding unit selected from the group of guiding units, consisting of said first guiding unit and said second guiding unit;

said first longitudinal axis and said second longitudinal axis intersecting in proximity of said symptomatic site, wherein said cannula-linking mechanism comprises at least one first locking member installed on said first cannula and a second locking member installed on all cannulae other than said first cannula, said second locking member being engaged with said at least one first locking member in a point of linking with a limited freedom of movement with respect to said at least one first locking member in the direction of said first longitudinal axis and with rotation around said point of linking.

2. The multiportal device of claim 1, wherein at least one of said first cannula and said at least a second cannula has stabilizing means for stabilizing a position of said first cannula and of said at least a second cannula after insertion thereof into said symptomatic site.

3. The multiportal device of claim 2, wherein said stabilizing means comprises a helical projection on at least one of said first cannula and on said at least a second cannula.

4. The multiportal device of claim 1, wherein said first cannula and said at least a second cannula have markers for aligning said at least one first locking member with said second locking member.

5. The multiportal device of claim 1, wherein said at least one arm has a shape of an arch with a center of said arch in a proximity of said symptomatic site.

6. The multiportal device of claim 1, wherein said first cannula has a first window at said distal end of said first cannula, said at least one first locking member comprises a rod spring-loaded inside said first cannula and moveable in the direction of said first axis, said rod having a normal position, in which said rod overlaps said first window, and a pull-up position, in which said rod is raised above said first window, said at least a second cannula having a second window at said distal end of said at least a second cannula, said second locking member comprises a spring-loaded loop having a normal position, in which said loop is positioned above said second window inside said at least a second cannula and a push-down position, in which said loop is aligned with said second window and protrudes radially outwardly therefrom into said first cannula through said first window to an extent that said rod in said normal position can be inserted into said loop.

7. The multiportal device of claim 6, wherein at least one of said first cannula and said at least a second cannula has stabilizing means for stabilizing a position of said first cannula and said at least a second cannula after insertion thereof into said symptomatic site.

8. The multiportal device of claim 7, wherein said stabilizing means comprises a helical projection on at least one of said first cannula and said at least a second cannula.

9. The multiportal device of claim 6, wherein at least one arm has a shape of an arch with a center of said arch in a proximity of said symptomatic site.

10. The multiportal device of claim 6, wherein said first cannula and said at least a second cannula have markers for aligning said first window with said second window.

11. The multiportal device of claim 10, wherein said markers comprise projections formed on said proximal end of said first cannula and on said proximal end of said at least a second cannula.

12. The multiportal device of claim 5, wherein said means for riding along said at least one arm comprise a plurality of rollers rotationally secured to said second guiding unit for rolling over said at least one arm.

13. The multiportal device of claim 12, wherein said means for riding along said at least one arm comprise a third clamping mechanism for securing said second guiding unit on said at least one arm.

14. The multiportal device of claim 5, wherein said at least one arm has an angular scale.

* * * * *